United States Patent
Novitski

(10) Patent No.: US 10,954,209 B1
(45) Date of Patent: *Mar. 23, 2021

(54) ACETYLATION OF CANNABINOIDS USING SULFURIC ACID CATALYST

(71) Applicant: Nextleaf Solutions Ltd., Coquitlam (CA)

(72) Inventor: David Novitski, Burnaby (CA)

(73) Assignee: Nextleaf Solutions Ltd., Vancouver (CA)

( * ) Notice: Subject to any disclaimer, the term of this patent is extended or adjusted under 35 U.S.C. 154(b) by 78 days.

This patent is subject to a terminal disclaimer.

(21) Appl. No.: 16/571,146

(22) Filed: Sep. 15, 2019

(51) Int. Cl.
*C07D 311/80* (2006.01)
*B01D 3/14* (2006.01)
*B01D 11/04* (2006.01)

(52) U.S. Cl.
CPC .............. *C07D 311/80* (2013.01); *B01D 3/14* (2013.01); *B01D 11/0488* (2013.01); *B01D 11/0492* (2013.01); *B01D 2257/70* (2013.01)

(58) Field of Classification Search
CPC .... C07D 311/80; B01D 3/14; B01D 11/0488; B01D 11/0492; B01D 2257/70
See application file for complete search history.

(56) References Cited

U.S. PATENT DOCUMENTS 10,569,189 B1 * 2/2020 Pal ...................... C07D 311/82

OTHER PUBLICATIONS

SkunkPharm, THC Acetate. Retrieved from https://skunkpharmresearch.com/thc-acetate/ on Jun. 17, 2020.

* cited by examiner

*Primary Examiner* — Timothy R Rozof
(74) *Attorney, Agent, or Firm* — Damien G. Loveland

(57) ABSTRACT

A process for producing THC-O-acetate using a succession of distillation, salting-out assisted liquid-liquid extractions (SALLEs), and solvent recovery techniques. Tetrahydrocannabinol (THC) in *Cannabis* oil reacts with acetic anhydride with hexane and under reflux to produce THC-O-acetate and acetic acid using sulfuric acid as a catalyst. The resulting crude product is distilled and subjected to a SALLE with hexane followed by a SALLE with petroleum ether, before being distilled again in order to obtain a refined, THC-O-acetate product.

20 Claims, 7 Drawing Sheets

ACETYLATION OF CANNABINOIDS USING SULFURIC ACID CATALYST

TECHNICAL FIELD

This invention relates to a process for the acetylation of neutral cannabinoids in *Cannabis* oil. More specifically, it relates to a process for acetylating tetrahydrocannabinol (THC) to form THC-O-acetate using a sulfuric acid catalyst, and subsequent refinement and purification of the THC-O-acetate using salting-out assisted liquid-liquid extraction (SALLE) and distillation techniques.

BACKGROUND

Extracted *Cannabis* products are attracting more consumers where *Cannabis* is legalized due to the higher potency of their therapeutic and psychoactive properties. As a consequence, sales of extracts are growing faster than the sales of dried *Cannabis*. Therefore, the elaboration of new extracted *Cannabis* products is important for the growth of the *Cannabis* industry.

For producing these new *Cannabis* products, industries are developing new processes in order to isolate or alter the effects of the active ingredients naturally found in *Cannabis* plants.

This background is not intended, nor should be construed, to constitute prior art against the present invention.

SUMMARY OF INVENTION

*Cannabis* products are created in such a way that a high content of psychoactive substances or prodrugs in these products is achieved. One of these prodrugs is THC-O-acetate, the structure of which is represented in FIG. 1. Compared to THC, this substance is considered to exhibit a higher potency of psychoactive power after being metabolized into THC. Also, there is a longer onset and a longer duration of its effect.

The present invention relates to a process for producing THC-O-acetate with a high degree of purity. For this, the process involves first the acetylation of THC with a sulfuric acid catalyst, then a succession of distillation, liquid-liquid extraction via SALLE, and solvent recovery techniques. Referring to FIG. 2, an embodiment of the reaction is shown with THC 1 reacting with acetic anhydride 2 to produce THC-O-acetate 3 and acetic acid 4.

Disclosed herein is a process for producing tetrahydrocannabinol acetate (THC-O-acetate) from *Cannabis* oil comprising: refluxing *Cannabis* oil with acetic anhydride at a temperature of 120-135° C. to form a crude product; distilling the crude product at a temperature of 90-125° C. to form a partially refined product; removing impurities from the partially refined product using a saline water solution wash with hexane; evaporating hexane from the partially refined product; removing further impurities from the partially refined product using a saline water solution wash with petroleum ether; and evaporating petroleum ether from the partially refined product.

Also disclosed herein is process for producing tetrahydrocannabinol acetate (THC-O-acetate) from *Cannabis* oil comprising: refluxing *Cannabis* oil with acetic anhydride, hexane and sulfuric acid at a temperature of 130-145° C. to form a crude product; removing impurities from the crude product to form a partially refined product using a saline water solution wash with hexane; evaporating hexane from the partially refined product; removing further impurities from the partially refined product using a saline water solution wash with petroleum ether; and evaporating petroleum ether from the partially refined product to result in a product that comprises THC-O-acetate.

BRIEF DESCRIPTION OF DRAWINGS

The following drawings illustrate embodiments of the invention, which should not be construed as restricting the scope of the invention in any way.

DESCRIPTION

Glossary

Cannabidiol (CBD) refers to a phytocannabinoid molecule that is obtained, through a decarboxylation process, from the CBDA found in *Cannabis* plants.

Cannabigerol (CBG) is a non-psychoactive cannabidiol usually present in smaller amounts in *Cannabis*.

Cannabinoids are a group of chemicals that act on cannabinoid receptors in the body, numerous of which are found in the *Cannabis* plant.

Cannabinol (CBN) is a mildly psychoactive cannabinoid found only in trace amounts in *Cannabis*, and is mostly found in aged *Cannabis*.

*Cannabis* distillate oil refers to an oil obtained from an extraction process conducted on raw *Cannabis* plant material using distillation.

*Cannabis* oil refers to an oil obtained from an extraction process conducted on raw *Cannabis* plant material.

Crude product refers to a mixture containing THC-O-acetate with solvents, impurities and/or reactants.

Partially refined product refers to a crude product that has gone through at least one refinement step or a product containing THC-O-acetate with traces of impurities, solvents and/or reactants.

SALLE refers to salting-out assisted liquid-liquid extraction, which is a solvent extraction technique involving an inorganic salt.

Tetrahydrocannabinolic acid (THCA) is a non-psychoactive cannabinoid found in *Cannabis*. THCA is the acidic form and precursor to THC. THCA converts to THC via decarboxylation when exposed to heat or sunlight.

THC or tetrahydrocannabinol refers to a phytocannabinoid molecule that is found in the *Cannabis* plant mostly in its acidic form, tetrahydrocannabinolic acid (THCA). THC levels in *Cannabis* plants are typically very low, e.g. <2%.

THC is known for its psychoactive effect when consumed or inhaled. It is more correctly known as delta-9-tetrahydrocannabinol.

THC-O-acetate refers to the compound of THC or tetrahydrocannabinol that has been transformed via an acetylation process.

Overview

Figure 1:
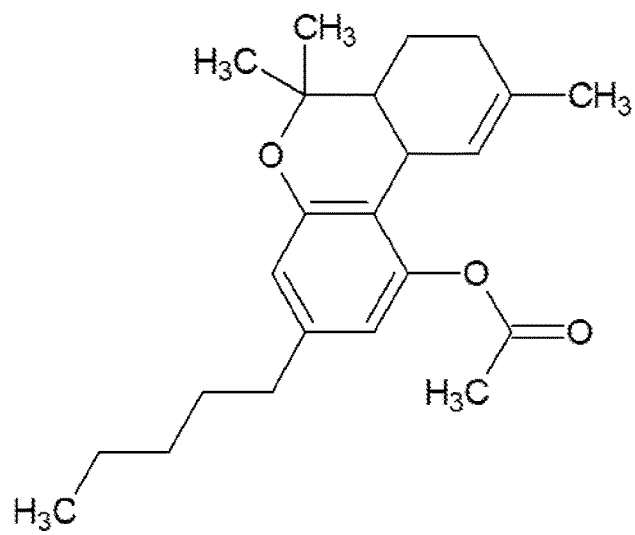
FIG. 1 is a drawing representing the chemical structure of THC-O-acetate.
Figure 2:
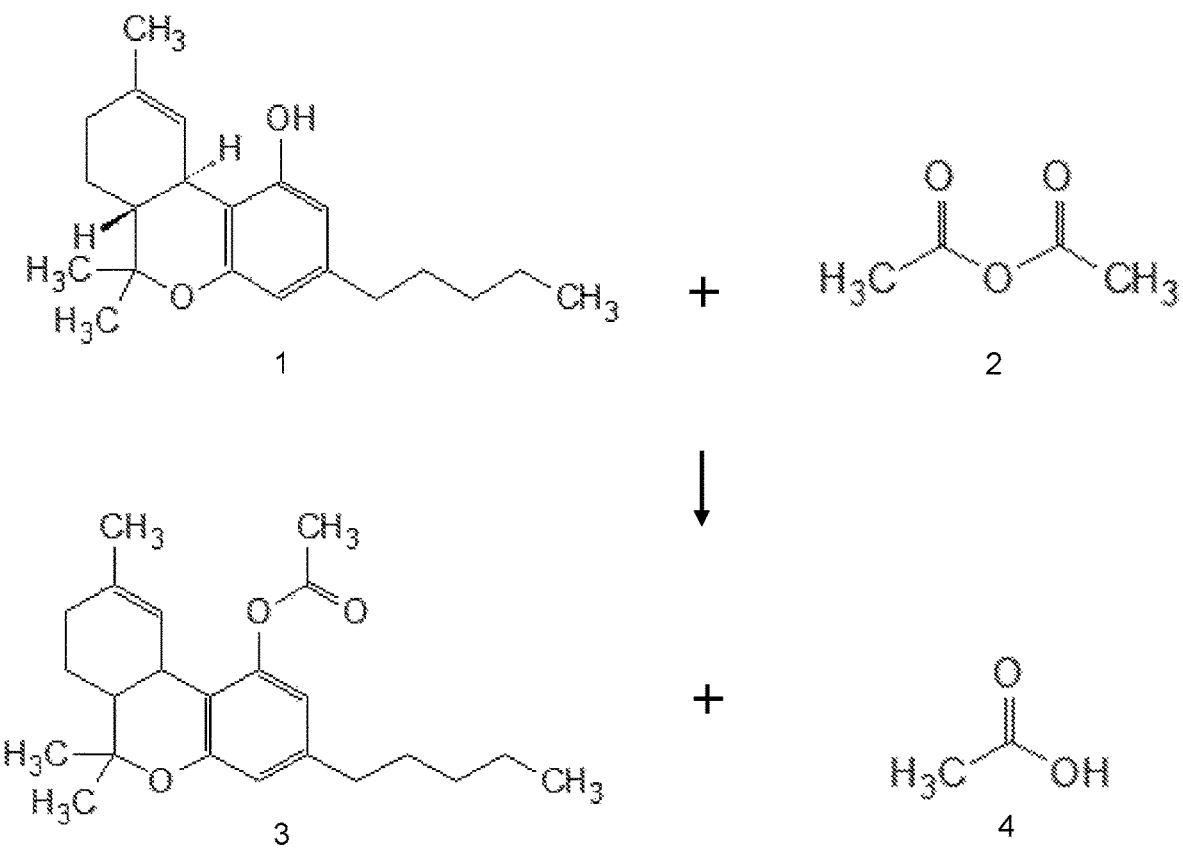
FIG. 2 is a drawing representing the reaction for producing THC-O-acetate.
Figure 3:
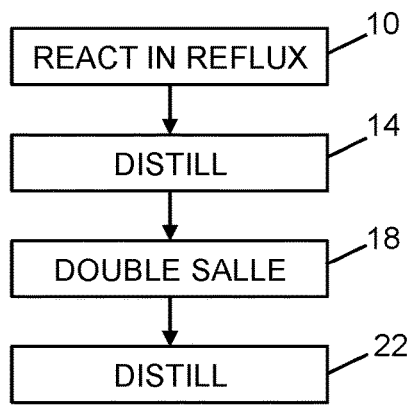
FIG. 3 is a high-level flowchart describing the key steps for producing THC-O-acetate according to an embodiment of the present invention.

Referring to FIG. 3 there are shown the key steps of the process. First, a reflux reaction between decarboxylated *Cannabis* oil, in which THC is present, and acetic anhydride occurs in step 10, resulting in a crude product of THC-O-acetate. In step 14, distillation is conducted on the crude product to form a partially refined product. Then, in step 18, the impurities are separated from the partially refined product using a double SALLE. In step 22, the resulting, partially refined product is distilled in order to obtain the THC-O-acetate in its refined form.

Exemplary Process

Figure 4:
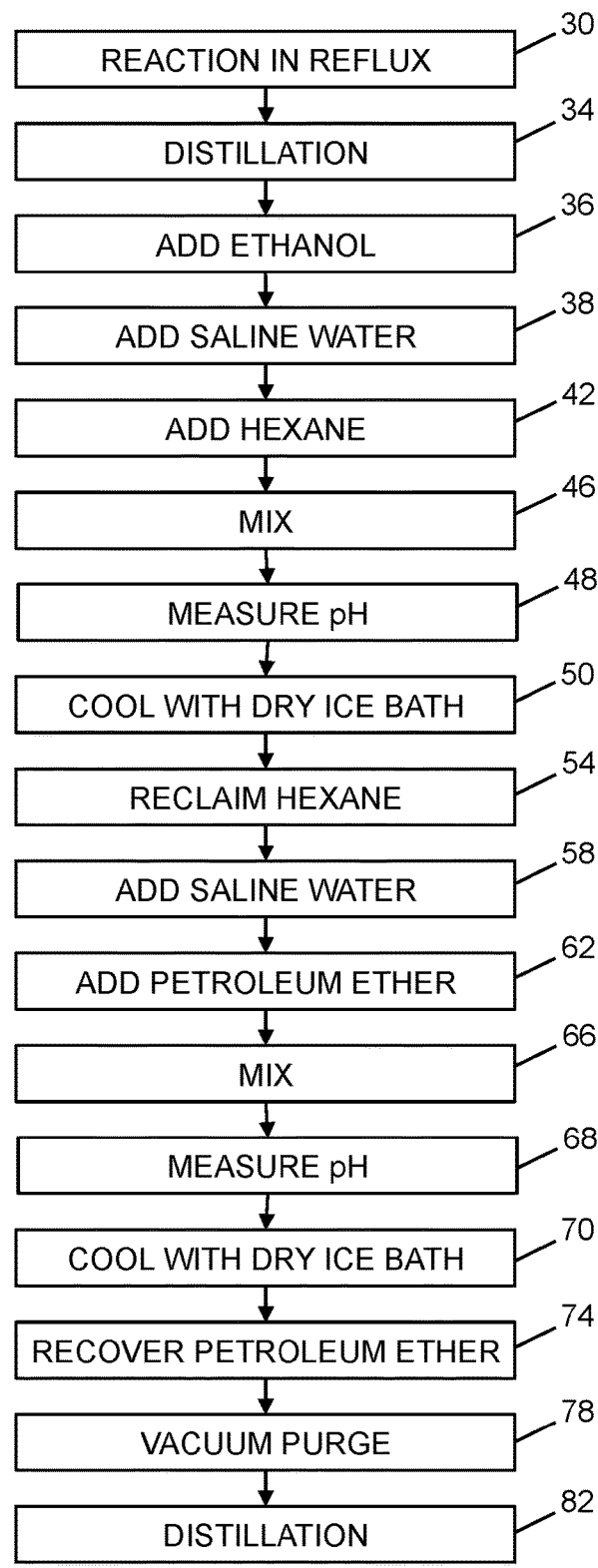
FIG. 4 is a detailed flowchart describing the steps for producing THC-O-acetate according to an embodiment of the present invention.

Referring to FIG. 4, there is shown in more detail the steps of the process for producing THC-O-acetate. In a first step 30, the *Cannabis* oil and acetic anhydride are mixed together in a heated flask equipped with a reflux condenser.

*Cannabis* oil used in the acetylation process typically includes 75-90% THC and 5% other cannabinoids. The remainder includes degradation products formed, for example, during a distillation process used in the production of the *Cannabis* oil. The 5% other cannabinoids are typically different for each batch and are based on the cannabinoid profile of the given strain. In general, this will be small amounts of CBD, CBG and CBN. These constituents can be analyzed using HPLC (High Performance Liquid Chromatography).

A quantity of 25-35 g of *Cannabis* oil and a volume of 150 mL of acetic anhydride are introduced into the flask. Nitrogen is introduced into the flask at a pressure of 0.5 psi (35 mbar) above atmospheric pressure for a period of 5-10 minutes in order to flush the flask free from oxygen, which would be detrimental to the reaction. The reflux reaction is conducted under a sealed, oxygen free atmosphere (e.g. nitrogen) at a temperature of 120-135° C. for a duration of 8-10 hours.

This reaction may also be carried out in the presence of any other inert gas. After the reaction, the resulting crude product is left to rest in the flask until it reaches ambient room temperature. In some embodiments, the reflux reaction is conducted using other inert gases.

In step 34, without having exposed the crude product to air, a distillation process is conducted on the crude product at a vacuum pressure of between 600 and 700 mmHg (800 and 940 mbar) and at a temperature of 90-125° C. Excess acetic anhydride is removed from the flask during this distillation process. At the end of the distillation process, a precipitate of the now partially refined product, in which the THC-O-acetate is present, is left in the flask. In step 36, ethanol is then added to the flask in order to dissolve the precipitate in order to facilitate its collection.

After that, in step 38, the resulting partially refined product is transferred to a separatory funnel. A saline water solution, prepared with 90-100 g of sodium chloride (NaCl) in 1000 mL of deionized water, is added into the separatory funnel. A volume of 500 mL of hexane is added to the separatory funnel in step 42. The contents inside the separatory funnel are then mixed vigorously in step 46. The use of inorganic salts in a liquid-liquid extraction process facilitates the formation of a two-phase system (with an organic phase and an aqueous phase) and the process is also known as SALLE. This phenomenon is used to enhance the extraction potency of a non-polar immiscible organic solvent such as hexane. Adding sodium chloride to the aqueous phase modifies the phase equilibrium in the mixture, the interaction between the liquid components, and therefore promotes a better separation between phases in addition to enhancing the extraction of the water-soluble impurities from the organic phase. In the present embodiment, the top, organic phase includes hexane and the partially refined THC-O-acetate while the bottom, aqueous phase includes ethanol and acetic acid, which is a byproduct of the reaction implemented in step 30.

In step 48, the pH of the aqueous phase is measured using a pH meter. The extraction is repeated, if necessary, one or more times by adding saline water solution to the partially refined product and hexane mixture until the aqueous phase formed reaches a pH value of 7±0.2. In some embodiments, the optical clarity of the aqueous phase is also measured in order to check that it is transparent.

The top phase or organic phase, which includes the partially refined product and hexane mixture, is retained and placed in a flask in a dry ice bath at a temperature of −70 to −80° C. for 1 hour in step 50. This allows any impurities that are present to settle to the bottom of the flask so that they can be discarded.

In step 54, the hexane is then recovered from the organic phase, now without the settled impurities, using a rotary evaporator set at a temperature of 60° C. with a vacuum pressure of 500-700 mm Hg (660-940 mbar). The recovery process is conducted until the hexane is substantially removed from the organic phase. When the majority or substantially all of the hexane has been removed, a viscous, partially refined product is left behind, with only traces of hexane, if any.

In step 58, a saline water solution, prepared with 90-100 g of sodium chloride (NaCl) in 1000 mL of deionized water, is added to a separatory funnel containing the viscous, partially refined product. In some embodiments, the quantity of sodium chloride is different. Then, a volume of 500 mL or more of petroleum ether is added to the separatory funnel in step 62. The mixture of the partially refined product, saline water solution and petroleum ether in the separatory funnel is vigorously mixed in step 66. During the agitation, any built-up pressure inside the separatory funnel is released periodically by opening the stopper of the separatory funnel. Then in step 68, the pH of the aqueous phase is measured following the same process as in step 48. The washing with the saline water solution is repeated one or more times until the pH of the resulting aqueous phase reaches the value of 7±0.2.

It is important to perform the SALLE with hexane before the SALLE with petroleum ether so that there is no need to be concerned about the ethanol content. The hexane performs better in forming distinct fractions when the mixture has a high alcohol content. If the SALLE with petroleum ether is run before the SALLE with hexane, the fractions will not be distinctly formed or sharply defined thus decreasing the efficiency of the SALLEs. The petroleum ether does not provide a distinct emulsion mid-layer if alcohol is present in the water in a high volume. It is important to have two SALLEs, both of which remove acetic acid. The point of performing the hexane wash is to remove ethanol as well as unreacted acetic anhydride from the partially refined product. If the petroleum ether SALLE is run before the hexane SALLE, ethanol traces will be not removed.

The top phase or organic phase, which includes the partially refined product and petroleum ether, is retained and placed in a flask in a dry ice bath at a temperature of −70 to −80° C. for a duration of 1 hour in step 70. This allows any further impurities that are present to settle to the bottom of the flask so that they can be discarded.

After that, in step 74, the petroleum ether is then removed from the organic phase, now without the further impurities, by placing the top phase in a rotary evaporator set at 60° C. with a vacuum pressure of 500-700 mmHg (660 and 940 mbar).

Then, in step 78, the partially refined product is placed in a vacuum oven set at a temperature of 80° C. for 1 hour in order to run a vacuum purge and remove any residual traces of petroleum ether or hexane. The result is THC-O-acetate as a partially refined product.

Finally, distillation, e.g. a short path distillation, is conducted with the partially refined product in order to separate out THC-O-acetate in step 82, as the final, refined product. Additionally, depending on the embodiment, other cannabinoid compounds are separated during this process.

Apparatus

Figure 5A:
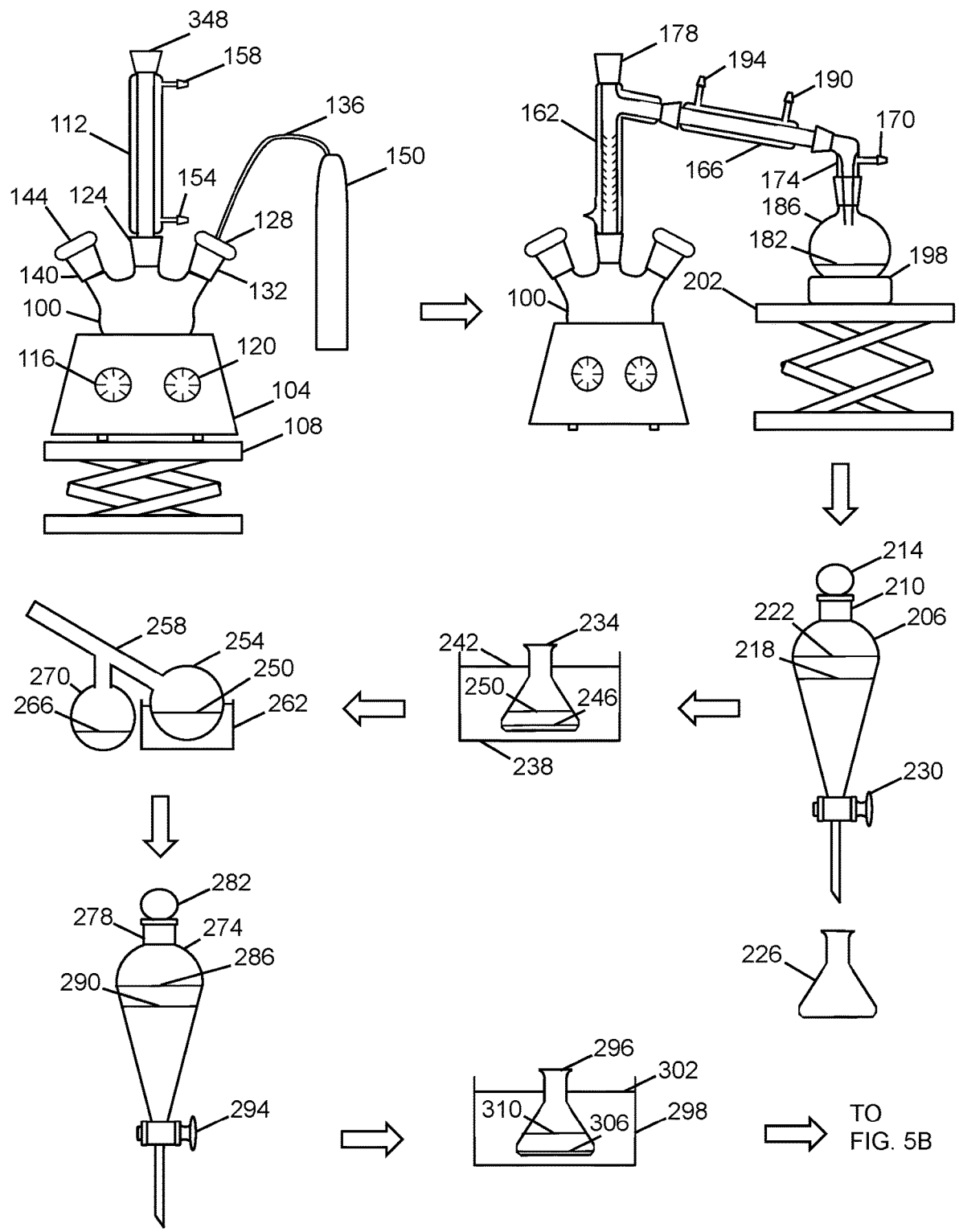
FIGS. 5A and 5B are a schematic diagram of the apparatus used to produce THC-O-acetate according to an embodiment of the present invention.

Referring to FIG. 5A, a three-neck round bottom flask 100 is placed on a heating mantle 104. In some embodiments, the heating mantle 104 with the bottom flask 100 is placed on a laboratory jack 108 to ensure that the heating mantle can be lowered while the assembly (i.e. a round bottom flask 100 attached to a reflux condenser 112) is held with one or more clamps. The temperature of the heating mantle 104 is controlled using the temperature dial 116. Agitation in the round bottom flask 100 is applied using a stirring magnet placed inside the flask and an agitation module controlled by dial 120 in the heating mantle 104. The speed of the agitation in the flask 100 can be controlled by turning the agitation dial 120 located on the heating mantle 104.

The first, central neck 124 of the round bottom flask 100 is attached to a reflux condenser 112, a gas inlet joint 128 or septa is hooked up to the second neck 132 to allow the introduction of nitrogen gas by means of a cannula 136. A non-represented clamp mounted on a retort stand is used to hold together the center neck 124 of the round bottom flask 100 and the reflux condenser 112. In addition, the clamp on the center neck 124 of the flask is used to hold the system when decreasing the height of the holding laboratory jack 108, when the position of the flask 100 over the heating mantle 104 requires to be adjusted (e.g. for decreasing the temperature in the system instantly).

The third neck 140 is used to introduce the reactants (i.e. 25-35 g of *Cannabis* oil and 150 ml of acetic anhydride). The quantity of *Cannabis* oil is based on the THC content (or other cannabinoid content) of the oil; therefore, in some embodiments, the quantities of *Cannabis* oil and acetic anhydride are different.

After introducing the reactants into the round bottom flask 100 (i.e. the reaction chamber), the inlet of the third neck 140 is plugged using a rubber stopper 144 to keep oxygen away from the round bottom flask. In order to remove the oxygen from the round bottom flask 100, nitrogen gas contained in a nitrogen source (e.g. gas tank or nitrogen line) 150 is introduced into the round bottom flask via the second neck 132 of the round bottom flask to purge oxygen from the system. The nitrogen source 150 is connected to the round bottom flask 100 via a cannula 136 inserted in a septa 128 mounted on the second neck 132 of the round bottom flask. This nitrogen is passed through at 35 mbar (0.5 psi) above atmospheric pressure or less for a period of 5-10 minutes until the round bottom flask 100 becomes oxygen-free. At that point, the round bottom flask 100 is completely purged with nitrogen, the introduction of nitrogen gas into the round bottom flask is stopped, and the round bottom flask is completely sealed by removing the cannula 136 from the septa 128, or by closing a valve on the nitrogen tank 150.

The reflux condenser 112 attached to the central neck 124 of the round bottom flask 100 is set at a temperature between −5 and −10° C. Polyethylene glycol is used as the coolant in the condenser 112. In some embodiments, a different coolant is used. The coolant enters the condenser 112 via inlet port 154 and exits the condenser via outlet port 158. The circulation of coolant is continuously carried out to maintain a temperature of −5 to −10° C. in the condenser 112. The reactants are continuously stirred in this case using a magnetic stir bar inside the flask 100 to allow constant mixing of reactants at a temperature of 120-135° C., set using the temperature dial 116 on the front panel of the heating mantle, for a duration of 8-10 hours. The agitation speed is set using the agitation dial 120 located on the front panel of the heating mantle 104.

Once the refluxing process is complete, the crude product is left in the bottom of the flask 100, which is not disconnected from the condenser 112 until it reaches ambient room temperature. After the flask 100 reaches ambient room temperature, the flask is attached to a distillation head (or Vigreux column) 162 and a condenser 166, ensuring that no oxygen comes into contact with the crude product, to further conduct a distillation process on the crude product.

Prior to the attachment of the round bottom flask 100 to the distillation head 162, the vacuum line and the cold trap attached to the system are purged by passing nitrogen gas through the inlet 170 of the still receiver 174. This process is conducted to prepare the reaction environment so that it is oxygen free. In some embodiments, a non-represented thermometer is inserted at the top 178 of the distillation head 162 in order to monitor the temperature at the entrance of the condenser 166. The distillation process is conducted at a vacuum pressure of between 600 and 700 mmHg (800 and 940 mbar) and at a temperature of 90-125° C. The excess acetic anhydride 182 is removed from flask 100 and collected in the flask 186 via the condenser 166 and the still receiver 174, leaving a precipitated partially refined product in the round bottom flask 100. A coolant enters the condenser 166 via inlet port 190 and exits the condenser via outlet port 194. The flask 186 in which the acetic anhydride is distilled is supported by a cork ring 198 on a laboratory jack 202.

A volume of 200 mL of ethanol is added to the round bottom flask 100 to dissolve the partially refined product precipitated onto the surface of the flask. In some embodiments, the volume of ethanol is different based on the obtained quantity of partially refined product. The amount of ethanol used should be a little as possible to dissolve the precipitate, since the ethanol will have to be removed later. The resulting partially refined product is further transferred into a separatory funnel 206 via its top opening 210 for a SALLE.

The saline water solution, prepared with 90-100 g of sodium chloride per 1000 mL of deionized water, is added into the separatory funnel 206 containing the partially refined product. In some embodiments, the quantity of sodium chloride dissolved in deionized water is different. A volume of 500 mL of hexane or more is added into the separatory funnel 206 containing the saline water and the partially refined product. A stopper 214 is placed at the top of the separatory funnel 206 before mixing the solution. The partially refined product along with saline water and hexane are vigorously mixed. After mixing, the liquid forms a bottom phase 218 and a top phase 222. The system might experience a pressure build-up during mixing, which can be released by opening the top opening 210 of the separatory funnel. The mixture in the separatory funnel 206 is allowed to stand until separation is observed.

The top phase 222 in the separatory funnel includes a mixture of the hexane and the partially refined product, while the bottom phase 218 includes the saline water with the impurities. If the phase separation is not observed, more hexane is added to the mixture. The separatory funnel 206 is then agitated again in order to separate the aqueous phase or bottom phase 218, which includes the saline water with the impurities, from the organic phase or top phase 222, which includes the hexane with the partially refined product. The saline water wash can be repeated until the bottom phase 218 is completely clear. The bottom phase, with the higher density, i.e. the aqueous phase 218 containing the saline water solution with the impurities is drained out from the separatory funnel 206 to a flask 226 by opening a stopcock 230 located at the bottom of the separatory funnel 206.

The top phase 222, which includes hexane and the partially refined product, is collected in a flask 234 and is placed in a bath 238 filled with dry ice 242 set at a temperature of −70 to −80° C. for a duration of 1 hour. This process allows impurities 246, if any, to settle in the bottom of the flask 234. The top layer 250 in the flask 234 is collected to next reclaim hexane.

The top layer 250, a mixture of hexane and the partially refined product, is collected is placed in a round bottom flask 254, and is heated in a rotary evaporator 258 set at a temperature of 60° C. via heated bath 262, with a vacuum pressure of 500-700 mmHg (660-940 mbar) to reclaim hexane from the mixture. The hexane 266 is collected in a flask 270. The reclaiming process is conducted until hexane is removed from the partially refined product, leaving a viscous, partially refined product behind, with only a trace amount, if any, of hexane.

A saline water solution, prepared with 90-100 g of NaCl per 1000 mL of deionized water, is added into a separatory funnel 274 into which the viscous, partially refined product has been transferred from the rotary evaporator. In some embodiments, the quantity of sodium chloride added to the deionized water in order to prepare the saline water solution is different. A volume of 500 mL or more of petroleum ether is added into the separatory funnel 274 containing the saline water solution and the partially refined product. The separatory funnel 274 is then closed using a stopper 282 before the mixing step. The partially refined product along with the saline water solution and petroleum ether are vigorously mixed. The system may experience a pressure build-up, which can be released by periodically opening the top opening 278 of the separatory funnel.

After mixing the solution in the separatory funnel 274, the mixture is allowed to stand until separation into two phases is observed. If the phase separation is not observed, more petroleum ether is added to the mixture.

The mixture separates into two phases i.e. the top phase 286, which includes the petroleum ether with the partially refined product, and the bottom phase 290, which includes the saline water solution with the impurities.

The saline water wash can be repeated until the bottom phase 290 is completely clear.

The top phase 286, which includes petroleum ether and the partially refined product, is collected in a flask 296 by opening the stopcock 294 at the bottom of the separatory funnel and first draining off the bottom phase 290. The flask 296, containing petroleum ether and partially refined product, is placed in a bath 298 containing dry ice 302 set at a temperature of −70 to −80° C. for a duration of 1 hour. This process allows the impurities 306, if any, to settle in the bottom part of the flask 296. The top layer 310, which includes petroleum ether and the partially refined product, is collected to further reclaim petroleum ether.

Figure 5B:
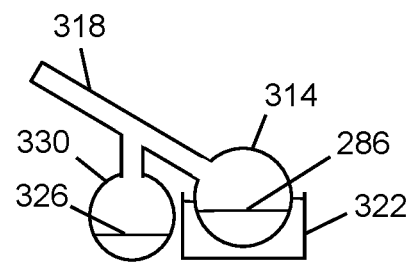
Figure 5B:
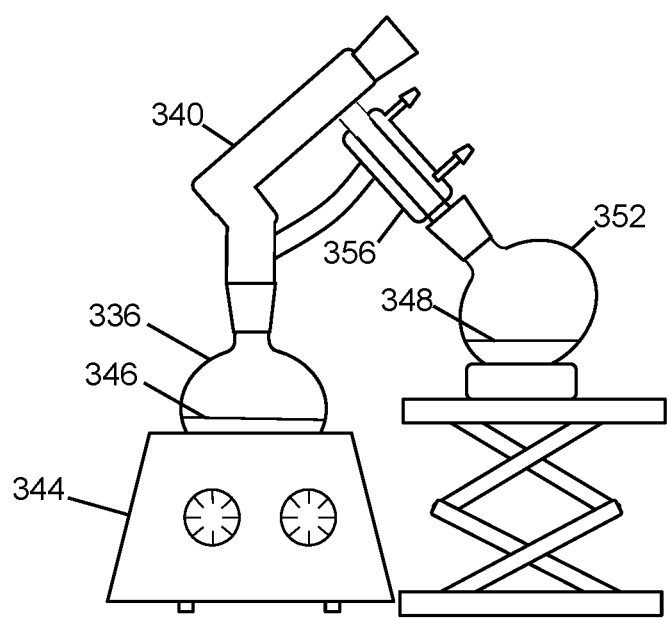

Referring to FIG. 5B, the top layer 286 is placed into a round bottom flask 314 and heated in a rotary evaporator 318 set at 60° C. using a heated bath 322 with a vacuum pressure of 500-700 mmHg (660-940 mbar) to reclaim petroleum ether 326 from the partially refined product and collect it in a round bottom flask 330. The recovery process is conducted until petroleum ether is substantially removed from the partially refined product, leaving a viscous, partially refined product behind, with only a trace amount, if any, of petroleum ether.

Then the viscous, partially refined product is placed on a tray in a vacuum oven 332 at 80° C. for a duration of 1 hour to purge the partially refined product of any residual petroleum ether or hexane.

The resulting partially refined product is then placed in a round bottom flask 336 and passed through a short path distillation unit 340 at 200-220° C. using a heating mantle 344 until THC-O-acetate as a refined product is separated from the partially refined product. The refined THC-O-acetate product 346 is collected in the flask 336 while the remainder 348 of the partially refined product containing other cannabinoids is collected in the flask 352 attached to a short length condenser 356.

In some embodiments, the *Cannabis* oil is replaced by a THC distillate.

Further Exemplary Process

Figure 6:
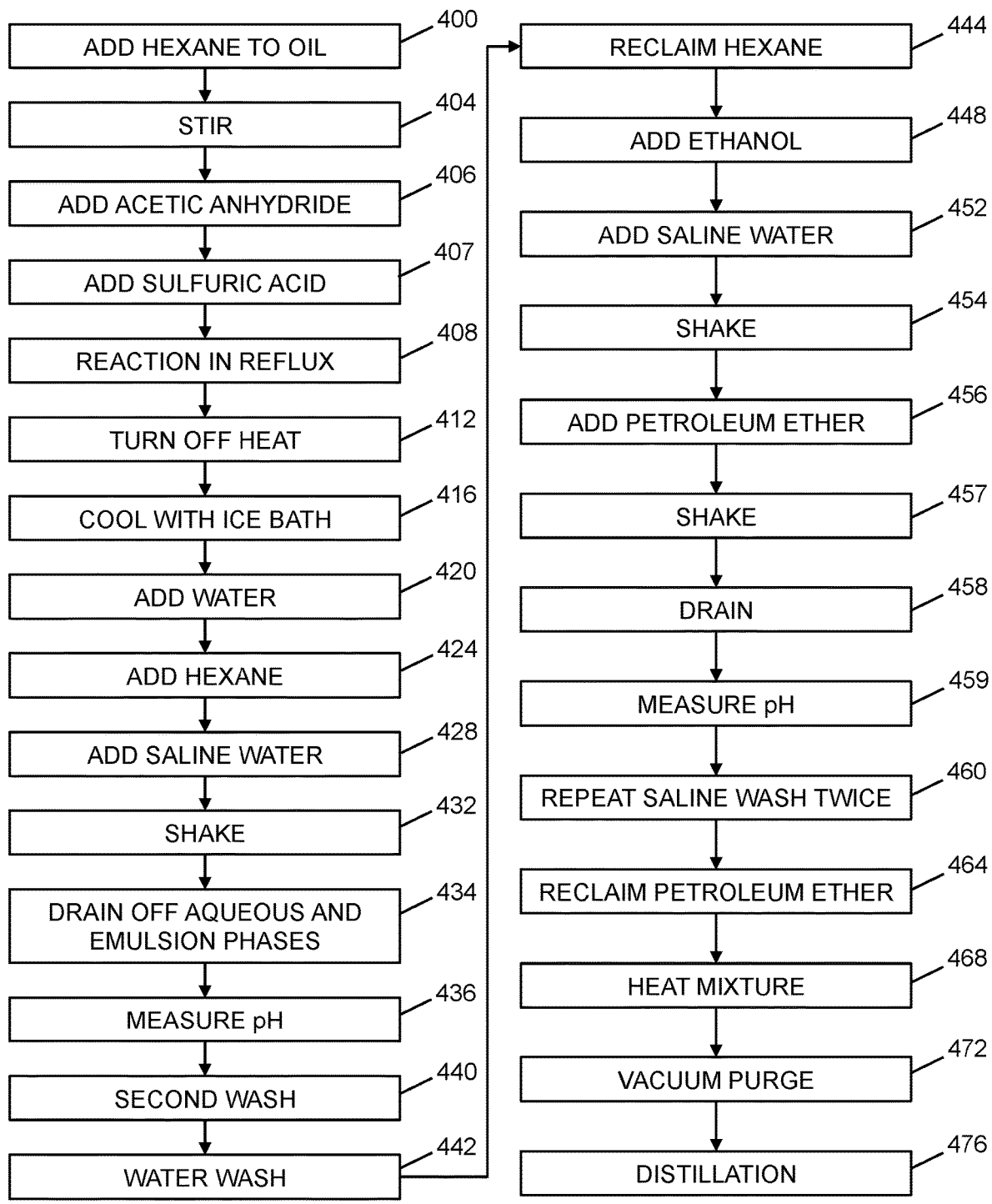
FIG. 6 is a detailed flowchart describing the steps for producing THC-O-acetate according to a further embodiment of the present invention.

Referring to FIG. 6, in step 400, an amount of 30±1 g of *Cannabis* oil (which may be THC distillate oil or more generally THC oil) and a volume of 45±1 mL of hexane is added to a 500 mL two-necked round bottom flask containing an egg-shaped magnetic stir bar. Hexane is used to dissolve the *Cannabis* oil and is a compatible solvent for the reflux reaction. The two-necked round bottom flask is placed on a heating mantle equipped with a stirrer in a fume hood. The flask containing the *Cannabis* oil and hexane is placed under agitation at room temperature and pressure until *Cannabis* oil is fully dissolved in step 404. In some embodiments, the heating mantle with a stirrer is replaced by separate elements such as a stir plate and a heating mantle.

After that, a reflux condenser is attached to the first neck of the two-necked round bottom flask. Water or other coolant is run through the reflux condenser at, for example, a minimum temperature of −5° C. Depending on whether coolant or water is used, however, the temperature will be different. More importantly is setting an adequate coolant flow rate through the condenser to ensure that fumes do not rise to the top of the condenser during the reaction. Generally during reflux the flow and/or temperature are set to whatever they need to be to prevent the escape of fumes from the condenser.

In the next step 406, a volume of 75±2 mL of acetic anhydride is added dropwise to the second neck of the two-necked round bottom flask, followed by the dropwise addition of a volume of 4±0.5 mL of sulfuric acid. The concentration of the sulfuric acid is typically 98%. Addition of the acetic anhydride and sulfuric acid occurs in some embodiments under agitation. The addition of sulfuric acid is exothermic and is carefully controlled to avoid overheating the vessel and creating a hazardous environment. Acetic anhydride is the acetylating agent for the *Cannabis* oil, while the sulfuric acid is used as a catalyst to drive the acetylation reaction. The temperature of the heating mantle is brought to 130-145° C. for 4-5 hours for the reflux reaction in step 408.

The heat is turned off in step 412 and then the two-necked round bottom flask with the resulting mixture is allowed to return to ambient room temperature. During step 412, the condenser and the stirrer are still operating.

Then, in step 416, the temperature of the two-necked round bottom flask is cooled down to a temperature of 4° C., i.e. cool because the next step is an exothermic reaction. In some embodiments, the temperature is set between 0 and 10° C. The temperature in the two-necked round bottom flask is monitored using a thermometer. For step 416, the heating mantle is replaced with an ice water bath, for example, while stirring continues in the two-necked round bottom flask.

In step 420, a volume of 30±5 mL of deionized water is slowly added to the two-necked round bottom flask, which is the first step of removing the remaining acid. The acid dissociates in the water and is removed in subsequent steps. The deionized water is added slowly to the flask because the reaction is exothermic. After that addition, a volume of 50±5 mL of hexane is added to the two-necked round bottom flask in step 424. The ice and water bath is removed in order to allow the mixture to return to ambient room temperature while the flask is still under agitation.

After that, the mixture is poured into a separatory funnel. A volume of 1000 mL of saline water solution (1-4 M NaCl) is added to the separatory funnel in step 428. The separatory funnel holding the mixture and the saline water solution is then shaken vigorously in step 432. During the agitation, any built-up pressure inside the separatory funnel is released periodically by opening the stopper of the separatory funnel. After the agitation, three distinct phases or layers are formed in the separatory funnel, which are, from bottom to top: aqueous, emulsion and organic. The layers are distinct and the thickness of the layers depends on the quality of the *Cannabis* oil. The aqueous and the emulsion phases are then drained off from the separatory funnel in step 434.

The pH of the drained aqueous phase is measured in step 436. A neutral pH of 7 indicates that the acid has been sufficiently removed from the mixture if the used water is an 18.2 Mohm water. In some embodiments, the pH that indicates the removal of the acid slightly differs depending on the quality of the water. In some embodiments, the optical clarity of the aqueous phase is measured in order to check that it is transparent. Optionally, the organic phase with the partially refined product and hexane mixture is placed in a flask in a dry ice bath in order to allow any impurities to settle at the bottom of the flask.

In step 440, a second wash is performed with 1000 mL of saline water solution (1-4 M NaCl), the aqueous and emulsion phases are drained off from the separatory funnel, and the pH of the aqueous phase is measured. Saline water washing is complete once the saline water wash pH is consistent. When the pH is consistent, a final wash with deionized water is applied in step 442.

Then, the organic phase remaining in the separatory funnel is transferred into another round bottom flask. The round bottom flask is placed into a rotary evaporator in order to reclaim all or substantially all of the hexane from the mixture in step 444.

In step 448, the mixture is dissolved by adding a volume of 200±5 mL of ethanol to the round bottom flask.

The mixture is transferred into a separatory funnel. A volume of 750 mL of saline water solution (1-4 M NaCl) is added to the separatory funnel holding the mixture in step 452 and then shaken vigorously in step 454.

A volume of 300±5 mL of petroleum ether is added to the separatory funnel in step 456. Then, the funnel is shaken vigorously in step 457 in order to separate the mixture into two distinct phases, which are, from bottom to top: aqueous and organic. The aqueous phase is drained off from the separatory funnel in step 458. There is no emulsion layer as it has been discarded during the saline wash with hexane. The pH of the aqueous phase is measured after the wash, in step 459.

In step 460, the saline water wash is repeated at least two more times with a solution of saline water (1-4 M NaCl) by adding a volume of 750 mL saline water each time. After each saline water wash, the aqueous phase is drained off from the separatory funnel. The pH of the aqueous phase is measured after each wash. In some embodiments, the saline water wash is repeated multiple times until the measured pH exhibits little or no variation. A significant fluctuation of the pH value between each wash indicates that the acid is still in the organic layer and the process is not finished. When the pH is consistent to within the desired tolerance, no more saline water washing is needed.

The remaining organic phase in the separatory funnel is then transferred into a round bottom flask. The round bottom flask is placed in the rotary evaporator in order to reclaim a majority of the petroleum ether from the mixture in step 464. Just enough petroleum ether is left in the flask to maintain the mixture as a non-viscous liquid so that it can be easily poured or otherwise transferred later.

Then the mixture is poured into a 250 mL flat bottom boiling flask. The flat bottom boiling flask is placed on a hot plate set at a temperature between 30° C. and 40° C. in order to evaporate the remaining petroleum ether from the mixture in step 468.

In step 472, the flask is placed in a vacuum oven set at a temperature of 80° C. with a vacuum of 30 mm Hg for 3 hours, to remove traces of petroleum either or hexane.

After that, the mixture is processed via a short path distillation with a temperature set between 200° C. and 220° C. in step 476, in order to separate out THC-O-acetate as the final, refined product.

Further Apparatus

Figure 7A:
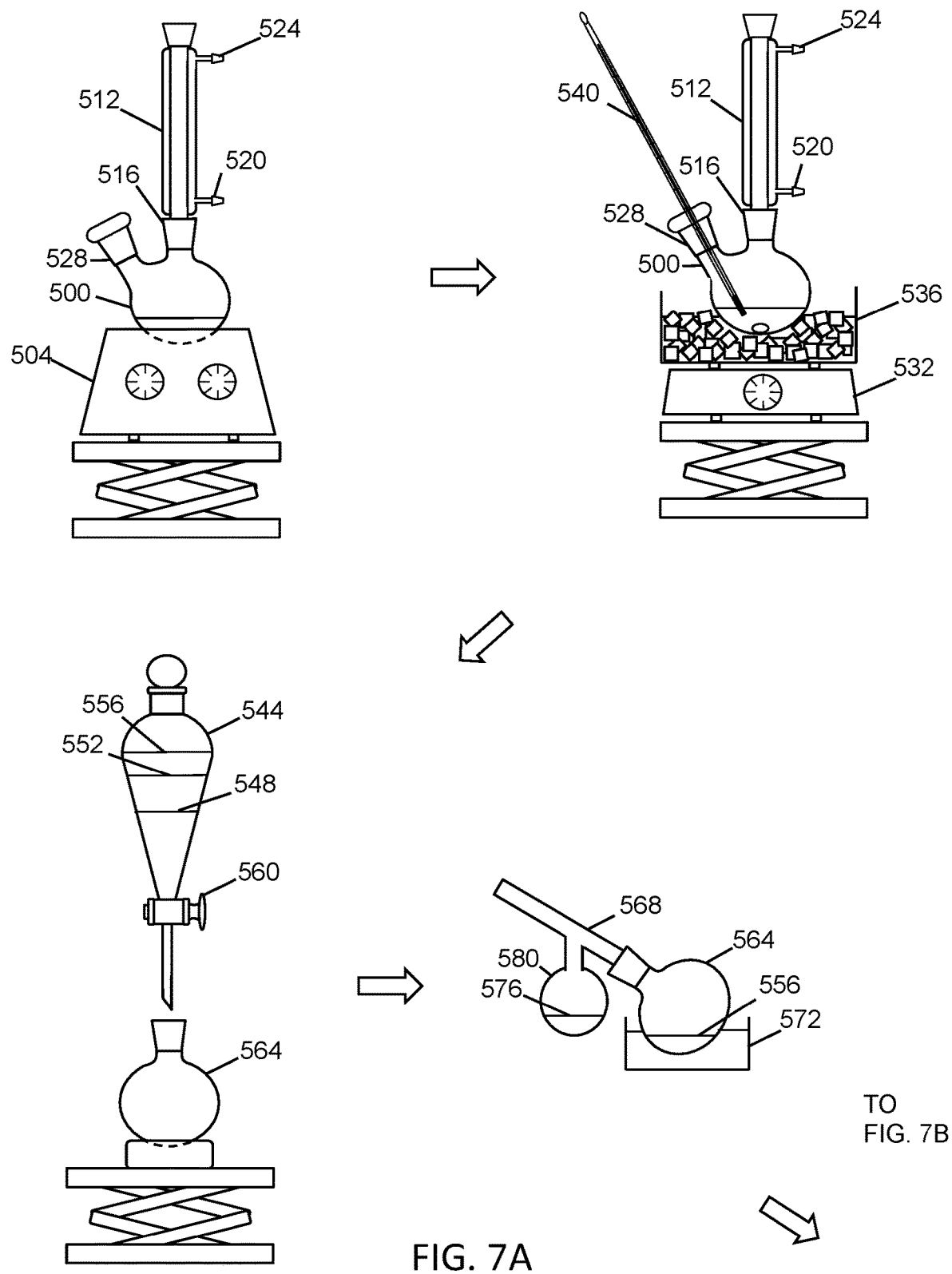
FIGS. 7A and 7B are a schematic diagram of the apparatus used to produce THC-O-acetate according to the further embodiment of the present invention.
Figure 7B:
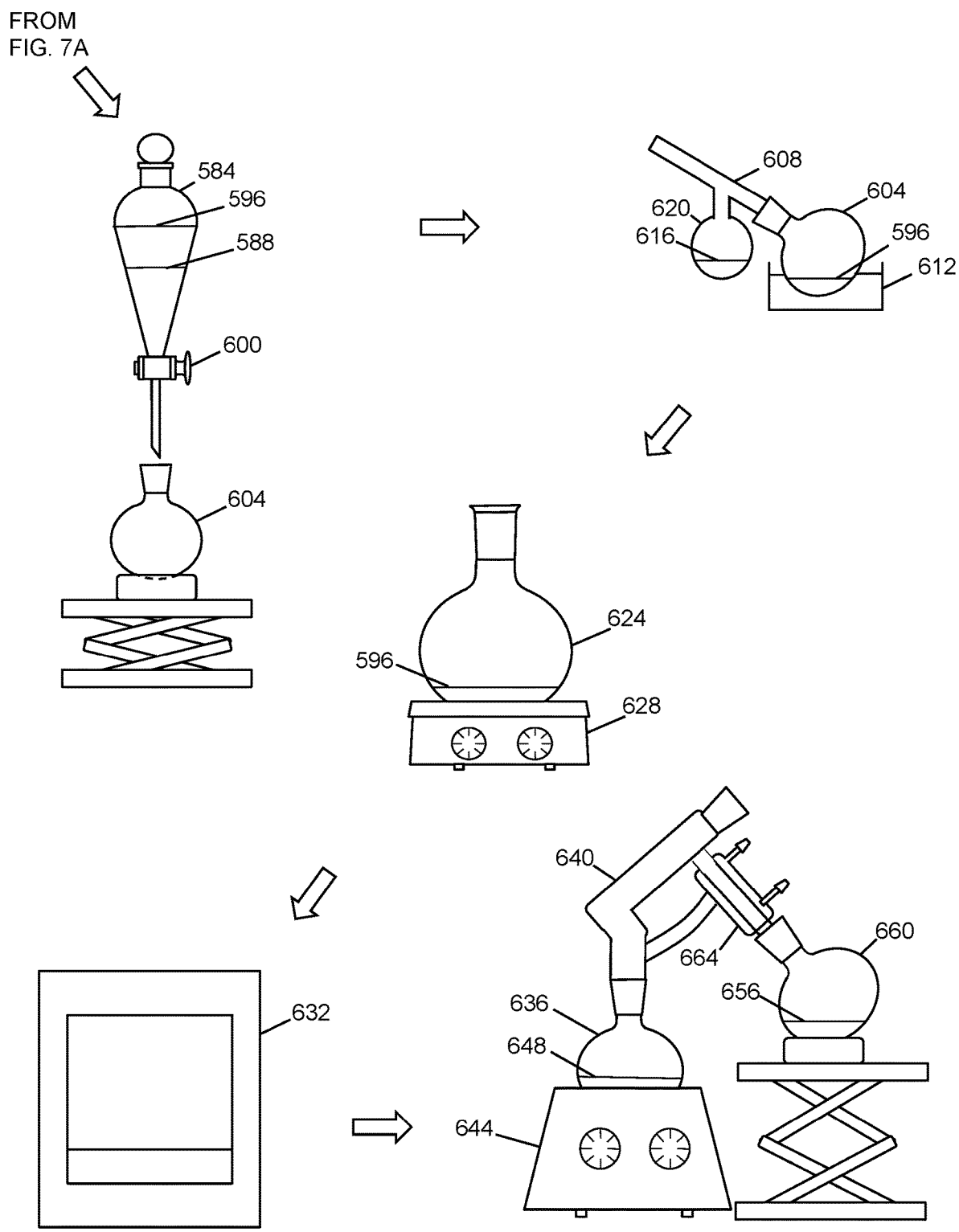

Referring to FIG. 7A, an amount of 30 g of *Cannabis* oil and 45±1 mL of hexane is added to a 500 mL two-necked round bottom flask 500 containing an egg-shaped magnetic stir bar. The two-necked round bottom flask 500 is placed on a heating mantle 504 equipped with a stirrer. The content of the two-necked round bottom flask 500 is stirred until the *Cannabis* oil is fully dissolved in hexane.

In some embodiments, the heating mantel 504 does not have a stirring function. In this case, the heating mantel 504 is placed under the two-necked round bottom flask 500 with a stir plate below the mantel.

A reflux condenser 512 is attached to the first neck 516 of the two-necked round bottom flask 500. Water or coolant is run through the reflux condenser 512 set to a temperature of a minimum of −5° C., or otherwise to prevent fumes escaping from the condenser. The water or coolant is introduced into the reflux condenser 512 via an inlet port 520 located at the bottom of the reflux condenser. The water is released from the reflux condenser 512 via an outlet port 524 located at the top of the reflux condenser.

A volume of 75±2 mL of acetic anhydride is added dropwise to the mixture via the second neck 528 of the two-necked round bottom flask 500. Then, a volume of 4±0.5 mL of sulfuric acid is added dropwise to the mixture via the second neck 528 of the two-necked round bottom flask 500. The temperature of the heating mantle 504 is brought to around 130-145° C. for 4-5 hours while stirring the contents of the flask 500.

The heat of the heating mantle 504 is turned off and then the temperature in the two-necked round bottom flask 500 is allowed to return to ambient room temperature. During that step, the reflux condenser 512 and the stirrer are still operating.

Then, the temperature of the two-necked round bottom flask 500 is cooled down to a temperature of 4° C. In some embodiments, the flask 500 is cooled down to a temperature of 0-10° C. The heating mantle 504 is replaced by a stirring plate 532 and an ice water bath 536, while the flask 500 is still under agitation. The temperature in the two-necked round bottom flask 500 is monitored using a thermometer 540 mounted in the second neck 528 of the two-necked round bottom flask 500.

A volume of 30±5 mL of deionized water is slowly added to the two-necked round bottom flask 500 via the second neck 528 of the flask. After that addition, a volume of 50±5 mL of hexane is added to the two-necked round bottom flask 500 via the second neck 528 of the flask. The ice water bath 536 is removed in order to allow the mixture to return to ambient room temperature while stirring.

After that, the mixture is poured into an appropriately sized separatory funnel 544. A volume of 1000 mL of saline water (1-4 M NaCl) is added to the separatory funnel 544. The separatory funnel 544 with the mixture and the saline water is then shaken vigorously. After the agitation, three distinct layers are formed in the separatory funnel 544, which are, from bottom to top: water 548, emulsion 552, organic 556.

Then, the water and the emulsion layers 548 and 552 are drained off from the separatory funnel 544 by opening the stopcock 560 of the separatory funnel. After that, the pH of the drained water is measured.

A second wash is performed with 1000 mL of saline water (1-4 M NaCl). The aqueous and emulsion layers are drained off from the separatory funnel and the pH of the aqueous phase is measured. The saline water washing is complete once the pH of the aqueous phase is consistent to within a desired tolerance. When the pH is consistent, a final wash with deionized water is performed.

The organic phase 556, which is a mixture of hexane and the partially refined product, remaining in the separatory funnel 544 is transferred into another round bottom flask 564. The round bottom flask 564 with the organic phase 556 is placed in a rotary evaporator 568 set at a temperature of 60° C. via a heated bath 572, with a vacuum pressure of 500-700 mmHg (660-940 mbar), in order to reclaim all or substantially all the hexane from the mixture to result in a viscous, partially refined product. The hexane 576 is collected in a round bottom flask 580.

The resulting viscous, partially refined product is dissolved by adding a volume of 200±5 mL of ethanol to the round bottom flask 564 in order to be transferred into a separatory funnel 584.

The mixture is transferred into a separatory funnel 584. A volume of 750 mL of saline water (1-4 M NaCl) is added to the separatory funnel 584. The separatory funnel 584 is shaken vigorously. A volume of 300±5 mL of petroleum ether is added to the separatory funnel 584. Then, the separatory funnel 584 is again shaken vigorously in order to separate the mixture into two distinct layers: aqueous 588 and organic 596.

The aqueous phase 588 is drained off from the separatory funnel 584. The saline water wash is repeated at least two more times with a saline water solution (1-4 M NaCl) by adding a volume of 750 mL saline water each time. After each saline water wash extraction, the aqueous layer is drained off from the separatory funnel 584 by opening the stopcock 600.

The remaining organic phase in the separatory funnel 584 is then transferred into a round bottom flask 604. The round bottom flask 604 is placed in a rotary evaporator 608 in order to reclaim petroleum ether from the mixture. The rotary evaporator 608 is set at a temperature of 60° C. via a heated bath 612, with a vacuum pressure of 500-700 mmHg (660-940 mbar), in order to reclaim most of the petroleum ether from the mixture, to result in a partially refined product dissolved in just enough petroleum ether to maintain it fluid enough for readily pouring or other transfer. The petroleum ether 616 is collected in a round bottom flask 620.

Enough petroleum ether is left in the flask 604 to keep the mixture as a non-viscous liquid in order to be easily transferred later. Then, the mixture 596 is poured into a 250 mL flat bottom boiling flask 624. The flat bottom boiling flask 624 is placed on a hot plate 628 set at a temperature between 30° C. and 40° C. in order to evaporate the remaining petroleum ether in the mixture.

The flat bottom boiling flask 624 is placed into a vacuum oven 632 set at a temperature of 80° C. with a vacuum pressure of 30 mm Hg for 3 hours to purge the partially refined product of any residual petroleum ether or hexane.

After that, the resulting partially refined product 596 is placed in a round bottom flask 636 and passed through a short path distillation unit 640 with a temperature set between at 200-220° C. using a heating mantle 644. The THC-O-acetate product 648 is collected in the flask 636 while the remainder 656 of the partially refined product 596 containing other cannabinoids is collected in the flask 660 attached to a short length condenser 664.

Variations

The above description relates to a bench-scale process, which can be scaled up by changing the quantities of reactants and the size and/or type of apparatus used.

Temperatures that have been given to the nearest degree include all temperatures within a range of ±0.5° C. of the given value. While in a specific embodiment, specific temperatures or temperature ranges have been given for various steps, such as condensation, it will be clear to one skilled in the art that other temperatures outside these ranges are also suitable.

Numbers are to be understood to be to the nearest last significant figure.

In some embodiments, after the distillation step, a column chromatography process is conducted on the mixture to isolate THC-O-acetate. If there is an issue concerning the other small percentage present in the distillate, a chromatography step can be added after the final distillation to separate other acetylated cannabinoids. The quantity of other acetylated cannabinoids depends on the quality of *Cannabis* oil used as reactant.

Various components of the apparatus may be connected to each other. For example, there may be a direct connection between the reflux components of the apparatus and the first distillation apparatus. Transfer from step to step in the process may therefore be made more efficient in other embodiments. Steps from one flowchart may be combined with another flowchart, and quantities used in one embodiment may be used in another embodiment.

Salts other than NaCl can be used for the SALLEs.

Wherein embodiments have been described in relation to *Cannabis* oil, the method equally applies to the use of *Cannabis* distillate oil as the starting oil.

Alternatives for the final distillation process include spinning band, wiped film and chromatography.

As an alternative, the whole process may be applied for the acetylation of cannabinoids other than THC such as CBD, CBG and CBN.

In general, unless otherwise indicated, singular elements may be in the plural and vice versa with no loss of generality.

Throughout the description, specific details have been set forth in order to provide a more thorough understanding of the invention. However, the invention may be practiced without these particulars. In other instances, well known elements have not been shown or described in detail and repetitions of steps and features have been omitted to avoid unnecessarily obscuring the invention. For example, various pumps, valves, jackets and lines are not shown for clarity. Accordingly, the specification and drawings are to be regarded in an illustrative, rather than a restrictive, sense.

It will be clear to one having skill in the art that further variations to the specific details disclosed herein can be made, resulting in other embodiments that are within the scope of the invention disclosed. All parameters, quantities, proportions and configurations described herein are examples only and may be changed depending on the specific embodiment. Accordingly, the scope of the invention is to be construed in accordance with the substance defined by the following claims.

The invention claimed is:

1. A process for producing tetrahydrocannabinol acetate (THC-O-acetate) from *Cannabis* oil comprising:
    refluxing *Cannabis* oil with acetic anhydride, hexane and sulfuric acid at a temperature of 130-145° C. to form a crude product;
    removing impurities from the crude product to form a partially refined product using a saline water solution wash with hexane;
    evaporating hexane from the partially refined product;
    removing further impurities from the partially refined product using a saline water solution wash with petroleum ether; and
    evaporating petroleum ether from the partially refined product to result in a product that comprises THC-O-acetate.

2. The process of claim 1, comprising:
    agitating, prior to the refluxing step, the *Cannabis* oil and hexane to result in a mixture; and
    adding, prior to the refluxing step, acetic anhydride and sulfuric acid dropwise to the mixture under agitation.

3. The process of claim 1, comprising:
    condensing the *Cannabis* oil and acetic anhydride during the refluxing step using a condenser with a coolant that has a flow rate selected to prevent fumes escaping from the condenser.

4. The process of claim 1 comprising, prior to the saline water solution wash with hexane:
    cooling the crude product after the refluxing step to a temperature of 0-10° C.; and
    adding deionized water to the crude product.

5. The process of claim 1, comprising adding ethanol to the partially refined product after evaporating the hexane.

6. The process of claim 1, comprising preparing saline water for the saline water solution washes with 90-100 g of sodium chloride per 1000 mL of deionized water.

7. The process of claim 1, comprising using 1-4 M NaCl solution for the saline water solution washes.

8. The process of claim 1, wherein:
    the saline water solution wash with hexane is repeated one or more times;
    the process comprises washing the partially refined product with deionized water after the saline water solution washes with hexane; and
    the saline water solution wash with petroleum ether is repeated two or more times.

9. The process of claim 1, wherein:
    the saline water solution wash with hexane uses a volume of hexane that is at least a twentieth of a volume of the saline water solution; and
    the saline water solution wash with petroleum ether uses a volume of petroleum ether that is at least two fifths of a volume of the saline water solution.

10. The process of claim 1, wherein each removing step comprises:
    agitating the partially refined product during the respective saline water solution wash;
    measuring that a bottom phase of a multiple-phase liquid resulting from the agitation has a pH of 7±0.2;
    discarding the bottom phase; and
    retaining a top phase of the multiple-phase liquid.

11. The process of claim 10 comprising adding more hexane or petroleum ether to the respective saline water solution wash if the pH of the bottom phase is previously measured to be not equal to 7±0.2.

12. The process of claim 1, wherein:
    evaporating the hexane is conducted using a rotary evaporator set at a temperature of 60° C. with a vacuum pressure of 660-940 mbar; and
    evaporating the petroleum ether is conducted using the rotary evaporator or another rotary evaporator set at a temperature of 60° C. with a vacuum pressure of 660-940 mbar.

13. The process of claim 1, comprising, after evaporating petroleum ether, heating the product to a temperature of 30-40° C. to remove traces of petroleum ether.

14. The process of claim 13, comprising further heating the product to a temperature of 80° C. at a vacuum pressure of 30 mm Hg for 3 hours to remove further traces of petroleum ether and hexane from the product.

15. The process of claim 14, comprising, after heating the product under vacuum, distilling the product at a temperature of 200-220° C. to remove compounds other than THC-O-acetate from the product, to form refined THC-O-acetate.

16. The process of claim 15, wherein distilling the product is conducted with a short path distillation device, a spinning band distillation device or a wiped film distillation device.

17. The process of claim 1, wherein the *Cannabis* oil comprises 75-90% THC.

18. The process of claim 1, wherein the oil is *Cannabis* distillate oil.

19. The process of claim 1, wherein the refluxing step is carried out for 4-5 hours.

20. The process of claim 1, wherein the ratio of *Cannabis* oil:acetic anhydride:hexane:sulfuric acid is 30±1 g:75±2 mL:45±1 mL:4±0.5 mL.

\* \* \* \* \*